United States Patent [19]

Tani et al.

[11] 4,273,719

[45] Jun. 16, 1981

[54] PROCESS FOR PREPARING 3,4,5,6-TETRAHYDROPHTHALIC ANHYDRIDES OR DERIVATIVES THEREOF

[75] Inventors: Shoji Tani; Kenji Nishio, both of Kyoto, Japan

[73] Assignee: New Japan Chemical Company, Ltd., Japan

[21] Appl. No.: 96,373

[22] Filed: Nov. 21, 1979

[51] Int. Cl.$^3$ ............................................. C07D 307/89
[52] U.S. Cl. ...................................................... 260/346.3
[58] Field of Search ...................................... 260/346.3

[56] References Cited

U.S. PATENT DOCUMENTS

| | | | |
|---|---|---|---|
| 2,764,597 | 9/1956 | Barney | 260/346.3 |
| 2,959,599 | 11/1960 | Bailey | 260/346.3 |
| 3,487,092 | 12/1969 | Cheng et al. | 260/346.3 |
| 3,819,658 | 6/1974 | Gormley et al. | 260/346.3 |
| 3,996,249 | 12/1976 | Corson et al. | 260/346.3 |
| 4,198,340 | 4/1980 | Ariga et al. | 260/346.3 |

FOREIGN PATENT DOCUMENTS 53-124242  10/1978  Japan .
54-48739   4/1979   Japan .

*Primary Examiner*—Richard Raymond
*Attorney, Agent, or Firm*—Larson and Taylor

[57] ABSTRACT

$\Delta^1$-THPA or a derivative thereof is prepared by isomerizing $\Delta^4$-THPA or a derivative thereof in the presence of (a) a palladium catalyst, and (b) an inorganic salt and/or a sulfur compound.

7 Claims, No Drawings

PROCESS FOR PREPARING 3,4,5,6-TETRAHYDROPHTHALIC ANHYDRIDES OR DERIVATIVES THEREOF

TECHNICAL FIELD

This invention relates to a process for preparing 3,4,5,6-tetrahydrophthalic anhydrides or derivatives thereof.

BACKGROUND ART

It is known that 3,4,5,6-tetrahydrophthalic anhydrides (hereinafter abbreviated as "$\Delta^1$-THPA") or methyl-substituted derivatives thereof are prepared usually by isomerizing 1,2,3,6-tetrahydrophthalic anhydrides (hereinafter abbreviated as "$\Delta^4$-THPA") or methyl-substituted derivatives thereof. Various processes for the isomerization are known, but they are still unsatisfactory in yield and the purity of the product. For example, the process in which an inorganic strong acid, such as phosphoric acid, phosphorus pentoxide, sulfuric acid or the like, is used as a catalyst has the drawback that the starting material undergoes marked oxidation during reaction, affording $\Delta^1$-THPA in low yields. Another conventional process in which palladium is used as a catalyst permits a disproportionation reaction in addition to the isomerization reaction, giving large amounts of phthalic anhydride and hexahydrophthalic anhydride as by-products to present difficulties in affording the desired product with a high purity. When producing the desired product with a high quality by these known processes, the reaction must be followed by distillation, recrystallization or like purifying procedure, which results in an increase in the number of steps as well as in cost and renders the process commercially unfavorable. Further if the yield is extremely low, it will be substantially impossible to resort to purification.

We have found that $\Delta^4$-THPA or a derivative thereof, when isomerized in the presence of a palladium catalyst and a specific compound, gives $\Delta^1$-THPA or a derivative thereof in a very high yield with a high purity.

An object of the invention is to provide a process for preparing $\Delta^1$-THPA or derivatives thereof with a high quality almost free from by-products, for example, due to disproportionation.

Another object of the invention is to provide a process for preparing $\Delta^1$-THPA or derivatives thereof in high yields with an easy procedure of purification.

DISCLOSURE OF INVENTION

The present invention provides a process for preparing $\Delta^1$-THPA or a derivative thereof represented by the formula

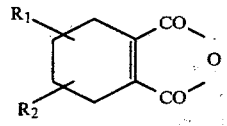

wherein $R_1$ and $R_2$ are each hydrogen or methyl, characterized in that $\Delta^4$-THPA or a derivative thereof represented by the formula

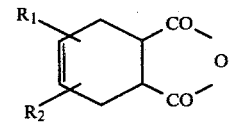

where $R_1$ and $R_2$ are as defined above is isomerized in the presence of (a) a palladium catalyst, and (b) an inorganic salt and/or a sulfur compound.

Examples of $\Delta^4$-THPA or derivatives thereof useful as the starting materials to be isomerized according to the invention are $\Delta^4$-THPA, 3-methyl-$\Delta^4$-THPA, 4-methyl-$\Delta^4$-THPA, 3,4-dimethyl-$\Delta^4$-THPA, 3,5-dimethyl-$\Delta^4$-THPA, 3,6-dimethyl-$\Delta^4$-THPA and 4,5-dimethyl-$\Delta^4$-THPA.

The palladium catalyst can be in the single form of metallic palladium but may preferably comprise a carrier for example of carbon, alumina, silica, asbestos or the like and about 0.1 to about 10% by weight, preferably about 1 to about 5% by weight, of palladium deposited on the carrier.

The isomerization reaction of the invention is conducted using the palladium catalyst conjointly with an inorganic salt and/or a sulfur compound.

Examples of useful inorganic salts are halides, nitrates, phosphates, etc. of alkali metals or alkaline earth metals. Typical of such salts are lithium chloride, potassium chloride, sodium chloride, magnesium chloride, calcium chloride, lithium bromide, potassium bromide, sodium bromide, potassium iodide, magnesium iodide, calcium iodide, lithium nitrate, potassium nitrate, sodium nitrate, magnesium nitrate, potassium phosphate, sodium phosphate, magnesium phosphate, etc. These inorganic salts, which may be added directly to the reaction system, can be used as deposited on a carrier, preferably on the same carrier as palladium.

The sulfur compounds to be used are sulfur per se, and organic or inorganic compounds containing sulfur in the molecule. These compounds exhibit high selectivity.

Useful sulfur-containing organic compounds include various examples, typical of which are represented by the formula $$R^1-S_x-R^2$$

wherein $R^1$ is $C_{1-20}$ alkyl, $C_{1-20}$ hydroxycarbonylalkyl, $C_{1-20}$ alkoxycarbonylalkyl, aryl or aralkyl, $R^2$ is $C_{1-20}$ alkyl, $C_{1-20}$ hydroxycarbonylalkyl, $C_{1-20}$ alkoxycarbonylalkyl, aryl or aralkyl, and x is an integer of 1 to 3. More specific examples of such compounds are methyl mercaptan, ethyl mercaptan, butyl mercaptan, lauryl mercaptan, dibutyl sulfide, dilauryl sulfide, p-tolyl mercaptan, benzyl mercaptan, dibenzyl sulfide, dibenzyl disulfide, dibenzyl trisulfide, thioglycolic acid, thiopropionic acid, diethyl thiodiacetate, dilauryl thiodipropionate, 4,4'-thiobis(3-methyl-6-t-butylphenol), etc. Alkali metal salts of mercaptans, thioglycolic acid and thiopropionic acid are also usable.

Other useful sulfur-containing organic compounds are represented by the formula $$C(CH_2R^3)_4$$

wherein $R^3$ is hydrogen, $C_{1-2}$ alkyl or $OCO(CH_2)_nSR^4$ and at least one of $R^3$ should be $OCO(CH_2)_nSR^4$ in which $R^4$ is hydrogen or $C_{1-20}$ alkyl, and n is an integer of 1 to 5. Examples of such compounds are trimethylolpropane trithioglycolate, pentaerythritol tetrathioglycolate, pentaerythritol-tetrakis-(3-laurylthiopropionate), etc. Alkali metal salts of these compounds are also usable.

Still other useful compounds include thiophene, 1,4-dithiodiene and like cyclic organic sulfur compounds, trialkyl($C_{1-20}$) trithiophosphite, tetraalkyl($C_{1-4}$)thiuram mono- or poly-sulfide, and p-toluenesulfonic acid or alkali metal salts thereof.

Useful sulfur-containing inorganic compounds are sulfides, sulfites, sulfates, thiosulfates, thiophosphates, thiocyanates, etc. of alkali metals or alkaline earth metals, exemplary of which are potassium sulfide, sodium sulfide, potassium sulfite, sodium sulfite, potassium sulfate, sodium sulfate, magnesium sulfate, calcium sulfate, sodium thiosulfate, sodium thiophosphate, sodium thiocyanate, etc.

Sulfur and these sulfur compounds may be added directly to the reaction system, or can be used as deposited on a carrier, preferably on the same carrier as palladium, in an amount of about 0.1 to about 10% by weight based on the carrier. Sulfur or the sulfur compound, depending on the concentration thereof, could act on the catalyst as a poison to inhibit the isomerization, to say nothing of disproportionation, so that the compound must be used in the reaction system in a strictly controlled concentration. Our research has revealed that the amount of sulfur or a sulfur compound suitable for use in the reaction system is in the range of about 1 to about 200 ppm, calculated as sulfur and based on $\Delta^4$-THPA or a derivative thereof used as the starting material. Larger amounts will inhibit the isomerization, whereas lesser amounts will entail poor selectivity.

For the reaction of this invention, it is preferable to use about 0.01 to about 5 parts (by weight, the same as hereinafter) of palladium (calculated as pure metal) and about 0.01 to about 50 parts of the inorganic salt per 1000 parts of $\Delta^4$-THPA or a derivative thereof used as the starting material. The sulfur compound, if used, should be used in the specified amount mentioned. According to this invention, either one of the organic salt and the sulfur compound is usable with the palladium catalyst, or both of them are usable with the catalyst.

With this invention, the starting material, the catalyst, etc. are placed into a reactor equipped with a stirrer, reflux condenser and nitrogen gas inlet and subjected to isomerization reaction in a nitrogen gas atmosphere. The reaction is conducted usually at about 130° to about 260° C., preferably at about 150° to about 200° C. The reaction time is usually about 4 to about 20 hours although not limited particularly.

The process of this invention affords the desired $\Delta^1$-THPA or derivative thereof in exceedingly high yield.

Separation of the catalyst from the reaction mixture by filtration or decantation affords the desired product as a finished product. When necessary, the product can be further purified as by distillation.

The invention will be described below with reference to examples.

EXAMPLES 1 TO 3

Predetermined amounts of $\Delta^4$-THPA serving as the starting material, a catalyst comprising palladium deposited on a carrier and an inorganic salt are placed into a four-necked flask equipped with a stirrer and a reflux condenser and then subjected to reaction in a nitrogen gas atmosphere to prepare $\Delta^1$-THPA. Table 1 shows the amounts, reaction conditions, results, etc.

The compounds obtained are identified by NMR, UV and IR absorption spectra. The proportions of the compounds in the product are determined by gas chromatography.

In the table, "HHPA" stands for hexahydrophthalic anhydride, "PA" for phthalic anhydride and "$\Delta^3$-THPA" for 1,2,3,4-tetrahydrophthalic anhydride.

TABLE 1

| Example | 1 | 2 | 3 |
|---|---|---|---|
| Amount of $\Delta^4$-THPA (%) | 100 | 100 | 100 |
| Catalyst carrier | Carbon | Alumina | Carbon |
| Amount of Pd deposit (%) | 5 | 5 | 5 |
| Amount of catalyst (g) | 0.3 | 0.3 | 0.1 |
| Inorganic salt | Sodium chloride | Sodium chloride | Potassium bromide |
| Amount of inorganic salt (g) | 0.2 | 0.1 | 0.2 |
| Reaction temp. (°C.) | 170 | 170 | 180 |
| Reaction time (h) | 9 | 8 | 7 |
| Yield (g) | 97 | 96 | 96 |
| Composition of product (%) | | | |
| $\Delta^1$-THPA | 93.0 | 92.0 | 95.5 |
| HHPA | 5.0 | 5.5 | 3.5 |
| PA | 2.0 | 2.5 | 1.0 |
| $\Delta^3$-THPA | Trace | Trace | Trace |

EXAMPLES 4 TO 6

$\Delta^4$-THPA is isomerized in the same manner as in Example 1 except that the catalyst used comprises palladium and an inorganic salt deposited on a carrier. Table 2 shows the results.

TABLE 2

| Example | 4 | 5 | 6 |
|---|---|---|---|
| Amount of $\Delta^4$-THPA (%) | 100 | 100 | 100 |
| Composition of catalyst | | | |
| Carrier | Carbon | Carbon | Carbon |
| Amount of Pd deposit (%) | 2 | 5 | 5 |
| Inorganic salt | Potassium chloride | Sodium chloride | Magnesium chloride |
| Amount of salt deposit (%) | 10 | 15 | 30 |
| Amount of catalyst (g) | 0.5 | 0.2 | 0.2 |
| Reaction temp. (°C.) | 180 | 180 | 190 |
| Reaction time (h) | 6 | 7 | 8 |
| Yield (g) | 96 | 97 | 97 |
| Composition of product | | | |
| $\Delta^1$-THPA | 94.0 | 96.5 | 92.0 |
| HHPA | 4.5 | 2.5 | 6.0 |
| PA | 1.5 | 1.0 | 2.0 |
| $\Delta^3$-THPA | Trace | Trace | Trace |

EXAMPLES 7 TO 11

$\Delta^4$-THPA is isomerized in the same manner as in Example 1 except that a sulfur compound is used in place of the inorganic salt. Table 3 shows the results.

TABLE 3

| Example | 7 | 8 | 9 | 10 | 11 |
|---|---|---|---|---|---|
| Amount of | 1000 | 1000 | 1000 | 1000 | 1000 |

TABLE 3-continued

| Example | 7 | 8 | 9 | 10 | 11 |
|---|---|---|---|---|---|
| $\Delta^4$-THPA (%) | | | | | |
| Catalyst carrier | Carbon | Carbon | Carbon | Carbon | Carbon |
| Amount of Pd deposit (%) | 5 | 5 | 5 | 5 | 5 |
| Amount of catalyst (g) | 2 | 2 | 2 | 2 | 2 |
| Sulfur compound | Lauryl mercaptan | Dibutyl sulfide | Sulfur | Sodium sulfide | Magnesium sulfate |
| Amount of S compound (g) | 0.02 | 0.01 | 0.01 | 0.01 | 2 |
| Reaction temp. (°C.) | 180 | 180 | 190 | 190 | 180 |
| Reaction time (h) | 12 | 12 | 10 | 12 | 10 |
| Yield (g) | 980 | 985 | 980 | 980 | 975 |
| Product composition (%) | | | | | |
| $\Delta^1$-THPA | 95.0 | 98.5 | 97.5 | 96.0 | 93.5 |
| HHPA | 3.0 | 1.2 | 2.0 | 3.0 | 5.0 |
| PA | 1.5 | Trace | 0.5 | 1.0 | 1.5 |
| $\Delta^3$-THPA | 0.5 | Trace | Trace | Trace | Trace |

EXAMPLES 12 TO 16

$\Delta^4$-THPA is isomerized in the same manner as in Example 1 except that the catalyst used comprises palladium and a sulfur compound deposited on a carrier. Table 4 shows the results.

TABLE 4

| Example | 12 | 13 | 14 | 15 | 16 |
|---|---|---|---|---|---|
| Amount of $\Delta^4$-THPA (%) | 1000 | 1000 | 1000 | 1000 | 1000 |
| Catalyst composition | | | | | |
| Carrier | Carbon | Carbon | Alumina | Carbon | Carbon |
| Amount of Pd (%) | 5 | 5 | 5 | 2 | 5 |
| Sulfur compound | Sulfur | Sulfur | Lauryl mercaptan | Sulfur | Calcium sulfate |
| Amount of compd. (%) | 2 | 1 | 1 | 0.5 | 10 |
| Amount of catalyst (g) | 2 | 2 | 1 | 4 | 2 |
| Reaction temp. (°C.) | 180 | 180 | 175 | 190 | 190 |
| Reaction time (h) | 12 | 8 | 8 | 8 | 8 |
| Yield (g) | 986 | 988 | 980 | 983 | 980 |
| Product composition (%) | | | | | |
| $\Delta^1$-THPA | 98.4 | 97.0 | 95.0 | 96.0 | 94.0 |
| HHPA | 1.1 | 2.0 | 3.0 | 2.8 | 4.0 |
| PA | 0.3 | 0.6 | 1.5 | 0.9 | 2.0 |
| $\Delta^3$-THPA | 0.2 | 0.4 | 0.5 | 0.3 | Trace |

EXAMPLES 17 TO 20

The procedure of Example 7 is repeated except that 3-methyl-$\Delta^4$-THPA or 4-methyl-$\Delta^4$-THPA is used as the starting material. Table 5 shows the results. The position of the methyl substituent in the starting material remains unchanged in the product obtained.

TABLE 5

| Example | 17 | 18 | 19 | 20 |
|---|---|---|---|---|
| Starting material | 3-Methyl-$\Delta^4$-THPA | 3-Methyl-$\Delta^4$-THPA | 4-Methyl-$\Delta^4$-THPA | 4-Methyl-$\Delta^4$-THPA |
| Amount of material (g) | 1000 | 1000 | 1000 | 1000 |
| Catalyst carrier | Carbon | Carbon | Carbon | Carbon |
| Amount of Pd deposit (%) | 5 | 5 | 5 | 5 |
| Amount of catalyst (g) | 2 | 2 | 2 | 2 |
| Sulfur compound | Dibutyl sulfide | Sodium sulfide | Lauryl mercaptan | Sulfur |
| Amount of S compound (g) | 0.011 | 0.01 | 0.01 | 0.01 |
| Reaction temp. (°C.) | 180 | 220 | 220 | 180 |
| Reaction time (h) | 12 | 6 | 6 | 12 |
| Yield (g) | 985 | 980 | 980 | 980 |
| Product composition (%) | | | | |
| 3- or 4-Methyl-$\Delta^1$-THPA | 93.0 | 95.0 | 90.0 | 85.0 |
| Methyl-HHPA | 4.0 | 3.0 | 5.0 | 7.0 |
| Others | 3.0 | 2.0 | 5.0 | 8.0 |

EXAMPLES 21 TO 24

The procedure of Example 12 is repeated except that 3-methyl-$\Delta^4$-THPA or 4-methyl-$\Delta^4$-THPA is used as the starting material. Table 6 shows the results.

TABLE 6

| Example | 21 | 22 | 23 | 24 |
|---|---|---|---|---|
| Starting material | 3-Methyl-$\Delta^4$-THPA | 3-Methyl-$\Delta^4$-THPA | 4-Methyl-$\Delta^4$-THPA | 4-Methyl-$\Delta^4$-THPA |
| Amount of material (g) | 1000 | 1000 | 1000 | 1000 |
| Catalyst composition | | | | |
| Carrier | Carbon | Carbon | Carbon | Carbon |
| Amount of Pd (%) | 5 | 5 | 5 | 5 |
| Sulfur compound | Sulfur | Sodium sulfide | Sulfur | Sodium sulfide |
| Amount of S compd. (%) | 1 | 1 | 1 | 1 |
| Amount of catalyst (g) | 2 | 2 | 2 | 2 |
| Reaction temp. (°C.) | 200 | 210 | 200 | 210 |
| Reaction time (h) | 10 | 8 | 10 | 8 |
| Yield (g) | 985 | 986 | 980 | 980 |
| Product composition (%) | | | | |
| 3- or 4-Methyl-$\Delta^1$-THPA | 93.0 | 92.0 | 89.0 | 87.0 |
| Methyl-HHPA | 4.0 | 5.0 | 6.0 | 8.0 |
| Others | 3.0 | 3.0 | 5.0 | 5.0 |

EXAMPLES 25 AND 26

The procedure of Example 1 is repeated except that a methyl-$\Delta^4$-THPA is used as the starting material. The results are shown in Table 7.

TABLE 7

| Example | 25 | 26 |
|---|---|---|
| Starting material | 3-Methyl-$\Delta^4$-THPA | 4-Methyl-$\Delta^4$-THPA |
| Amount of material (g) | 1000 | 1000 |
| Catalyst carrier | Carbon | Carbon |
| Amount of Pd deposit (%) | 5 | 5 |
| Amount of catalyst | 2 | 2 |

TABLE 7-continued

| Example | 25 | 26 |
|---|---|---|
| (g) | | |
| Inorganic salt | Sodium chloride | Sodium chloride |
| Amount of inorganic salt (g) | 2 | 2 |
| Reaction temp. (°C.) | 180 | 180 |
| Reaction time (h) | 8 | 8 |
| Yield (g) | 960 | 950 |
| Composition of product (%) | | |
| 3- or 4-Methyl-$\Delta^1$-THPA | 92.0 | 85.0 |
| Methyl-HHPA | 4.0 | 6.0 |
| Others | 4.0 | 9.0 |

EXAMPLES 27 AND 28

The procedure of Example 4 is repeated except that a methyl-$\Delta^4$-THPA is used as the starting material. The results are shown in Table 8.

TABLE 8

| Example | 27 | 28 |
|---|---|---|
| Starting material | 3-Methyl-$\Delta^4$-THPA | 4-Methyl-$\Delta^4$-THPA |
| Amount of material (g) | 1000 | 1000 |
| Composition of catalyst | | |
| Carrier | Carbon | Carbon |
| Amount of Pd deposit (%) | 5 | 5 |
| Inorganic salt | Sodium chloride | Sodium chloride |
| Amount of salt deposit (%) | 15 | 15 |
| Amount of catalyst (g) | 2 | 2 |
| Reaction temp. (°C.) | 180 | 180 |
| Reaction time (h) | 8 | 8 |
| Yield (g) | 970 | 960 |
| Composition of product (%) | | |
| 3- or 4-Methyl-$\Delta^1$-THPA | 94.0 | 88.0 |
| Methyl-HHPA | 4.0 | 5.0 |
| Others | 2.0 | 7.0 |

EXAMPLES 29 AND 30

The procedure of Example 1 is repeated except that 3,6-dimethyl-$\Delta^4$-THPA serving as the starting material, a catalyst comprising palladium as deposited on a carrier, and an inorganic salt or a sulfur compound are used. The results are shown in Table 9.

TABLE 9

| Example | 29 | 30 |
|---|---|---|
| Amount of starting material (g) | 1000 | 1000 |
| Catalyst carrier | Carbon | Carbon |
| Amount of Pd deposit (%) | 5 | 5 |
| Amount of catalyst (g) | 2 | 2 |
| Inorganic salt or sulfur compound | Sodium chloride | Dibutyl sulfide |
| Amount of salt or S compound (g) | 2 | 0.01 |
| Reaction temp. (°C.) | 190 | 190 |
| Reaction time (h) | 12 | 10 |
| Yield (g) | 950 | 960 |

TABLE 9-continued

| Example | 29 | 30 |
|---|---|---|
| Composition of product (%) | | |
| 3,6-dimethyl-$\Delta^1$-THPA | 89.0 | 90.0 |
| Dimethyl-HHPA | 7.0 | 5.0 |
| Others | 4.0 | 5.0 |

EXAMPLES 31 AND 32

The procedure of Example 1 is repeated except that 3,6-dimethyl-$\Delta^4$-THPA serving as the starting material and a catalyst comprising palladium, and an inorganic salt or sulfur compound deposited on a carrier are used. Table 10 shows the results.

TABLE 10

| Example | 31 | 32 |
|---|---|---|
| Amount of starting material (g) | 1000 | 1000 |
| Composition of catalyst | | |
| Carrier | Carbon | Carbon |
| Amount of Pd deposit (%) | 5 | 5 |
| Inorganic salt or sulfur compd. | Potassium chloride | Lauryl mercaptan |
| Amount of salt or S compd. (%) | 15 | 1 |
| Amount of catalyst (g) | 2 | 2 |
| Reaction temp. (°C.) | 180 | 180 |
| Reaction time (h) | 12 | 12 |
| Yield (g) | 960 | 970 |
| Composition of product (%) | | |
| 3,6-dimethyl-$\Delta^1$-THPA | 90.0 | 92.0 |
| Dimethyl-HHPA | 6.0 | 4.0 |
| Others | 4.0 | 4.0 |

Industrial Applicability

The $\Delta^1$-THPA compounds and derivatives thereof prepared by the process of this invention are useful as materials for agricultural and horticultural fungicides, herbicides, etc., as epoxy resin curing agents and also as materials for polyester resins.

We claim:
1. A process for preparing a 3,4,5,6-tetrahydrophthalic anhydride or a derivative thereof represented by the formula

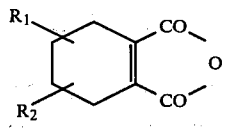

wherein $R_1$ and $R_2$ are each hydrogen or methyl, in high yields of high purity comprising isomerizing a 1,2,3,6,-tetrahydrophthalic anhydride or a derivative thereof represented by the formula

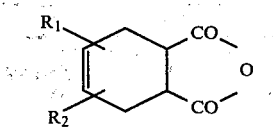

wherein $R_1$ and $R_2$ are as defined above in the presence of (a) a palladium catalyst, and (b) an inorganic salt and/or a sulfur compound.

2. A process as defined in claim 1 wherein the inorganic salt is a halide, nitrate or phosphate of an alkali metal or alkaline earth metal.

3. A process as defined in claim 1 wherein the sulfur compound is sulfur, a sulfur-containing organic compound or a sulfur-containing inorganic compound.

4. A process as defined in claim 1 wherein the sulfur-containing organic compound is at least one of compounds represented by the formula $$R^1-S_x-R^2$$

wherein $R^1$ is $C_{1-20}$ alkyl, $C_{1-20}$ hydroxycarbonylalkyl, $C_{1-20}$ alkoxycarbonylalkyl, aryl or aralkyl, $R^2$ is $C_{1-20}$ alkyl, $C_{1-20}$ hydroxycarbonylalkyl, $C_{1-20}$ alkoxycarbonylalkyl, aryl or aralkyl, and x is an integer of 1 to 3; compounds represented by the formula $$C(CH_2R^3)_4$$

wherein $R^3$ is hydrogen, $C_{1-2}$ alkyl or $OCO(CH_2)_nSR^4$ and at least one of $R^3$ is $OCO(CH_2)_nSR^4$ in which $R^4$ is hydrogen or $C_{1-20}$ alkyl, and n is an integer of 1 to 5; cyclic organic sulfur compounds including thiophene and 1,4-dithiodiene trialkyl($C_{1-20}$) trithiophosphite; tetraalkyl ($C_{1-4}$)thiuram mono- or poly-sulfide; and p-toluenesulfonic acid or alkali metal salts thereof.

5. A process as defined in claim 1 wherein the sulfur-containing inorganic compound is at least one of sulfides, sulfites, sulfates, thiosulfates, thiophosphates and thiocyanates of alkali metals or alkaline earth metals.

6. A process as defined in claim 1 wherein the inorganic salt is used in an amount of about 0.01 to about 50 parts by weight per 1000 parts by weight of the starting material.

7. A process as defined in claim 1 wherein the sulfur compound is used in an amount of about 1 to about 200 ppm calculated as sulfur and based on the starting material.

* * * * *